US008801436B2

(12) United States Patent
Arnold (10) Patent No.: US 8,801,436 B2
(45) Date of Patent: Aug. 12, 2014

(54) ORAL HYGIENE COMPOSITION AND APPARATUS AND METHOD

(75) Inventor: Michael Arnold, Beverly Hills, CA (US)

(73) Assignee: Carson Laboraotories, I, P., Inc., Las Vegas, NV (US)

( * ) Notice: Subject to any disclaimer, the term of this patent is extended or adjusted under 35 U.S.C. 154(b) by 87 days.

(21) Appl. No.: 12/061,493

(22) Filed: Apr. 2, 2008

(65) Prior Publication Data

US 2009/0253101 A1  Oct. 8, 2009

(51) Int. Cl.
*A61C 17/00* (2006.01)

(52) U.S. Cl.
USPC ............... 433/216; 433/215; 424/49; 424/53

(58) Field of Classification Search
USPC ............. 433/80, 215–216, 229; 424/43–58; 601/162–165
See application file for complete search history.

(56) References Cited

U.S. PATENT DOCUMENTS

| | | | | |
|---|---|---|---|---|
| 3,897,779 A * | 8/1975 | Hansen | | 128/203.15 |
| 3,976,223 A * | 8/1976 | Jass et al. | | 222/94 |
| 5,009,885 A | 4/1991 | Yarborough | | |
| 5,611,690 A | 3/1997 | Summers et al. | | |
| 5,804,165 A | 9/1998 | Arnold | | |
| 5,817,294 A | 10/1998 | Arnold | | |
| 5,965,110 A | 10/1999 | Arnold | | |
| 6,086,854 A | 7/2000 | Arnold | | |
| 6,413,500 B1 * | 7/2002 | Thorwaldson | | 424/49 |
| 6,419,906 B1 | 7/2002 | Xu et al. | | |
| 6,599,126 B1 | 7/2003 | Sale et al. | | |
| 6,620,405 B2 * | 9/2003 | Oxman et al. | | 424/45 |
| 6,635,272 B2 | 10/2003 | Leaderman | | |
| 6,958,144 B2 | 10/2005 | Montgomery | | |
| 7,060,253 B1 * | 6/2006 | Mundschenk | | 424/45 |
| 7,189,385 B2 * | 3/2007 | Montgomery | | 424/53 |
| 2004/0094151 A1 | 5/2004 | Speldrich | | |
| 2004/0197270 A1 * | 10/2004 | Mundschenk | | 424/45 |
| 2005/0048444 A1 * | 3/2005 | Creamer | | 433/215 |
| 2005/0214720 A1 * | 9/2005 | Milanovich et al. | | 433/215 |
| 2006/0171907 A1 * | 8/2006 | Scott et al. | | 424/53 |
| 2006/0231093 A1 * | 10/2006 | Burge et al. | | 128/203.15 |
| 2007/0189983 A1 * | 8/2007 | Gordon et al. | | 424/53 |
| 2008/0071233 A1 | 3/2008 | Ross | | |
| 2008/0175801 A1 * | 7/2008 | Ramji | | 424/53 |
| 2009/0108021 A1 * | 4/2009 | Hansen et al. | | 222/1 |

FOREIGN PATENT DOCUMENTS

JP    2002-045378    12/2002

OTHER PUBLICATIONS

Arnold, Michael J. et al., Effects of a Chewable Sodium Bicarbonate Tablet on Gingivitis, Bleeding, Plaque and Pathogenic Microflora, Spring 1996, p. 1-4.
Guidance document on Epidemiological and clinical studies on Tooth Whitening Products, SCCP, Mar. 28, 2006, p. 1-6.

(Continued)

*Primary Examiner* — Cris L Rodriguez
*Assistant Examiner* — Edward Moran
(74) *Attorney, Agent, or Firm* — Knobbe, Martens, Olson & Bear LLP (57) ABSTRACT

A method and accompanying apparatus that allows high concentrations of hydrogen peroxide for tooth whitening by use of an aerosol spray. The aerosol spray may be delivered through a mouthpiece that will direct the spray onto the teeth while inhibiting any escape of the spray to the lips and outside the moth. Also, in combination with antiplaque formulations, enhanced tooth whitening is effected.

3 Claims, 7 Drawing Sheets

(56) References Cited

OTHER PUBLICATIONS

Haywood, Van B., History, safety, and effectiveness of current . . . vital bleaching technique., Quintessence International, vol. 23, No. 7, 1992, p. 471-488.

Hydrogen Peroxide Solution, 30%, Material Safety Data Sheet from Vinquiry, Inc.

Material Safety Data Sheet, Eka Chemicals, Inc., http://www.ekamsds.com, Jul. 11, 2006, p. 1-7.

Miller, Samuel Charles et al., Hydrogen Peroxide and Sodium Perborate: Their Comparative Oral Irritant Action, Journal A.D.A and D. Cosmo, vol. 25, Dec. 1938, p. 1957-1973.

Newbrun, Ernest et al., Bactericidal Action of Bicarbonate Ion on Selected Periodontal Pathogenic Microorganism, Journal of Periodontology, vol. 55(11), Nov. 1984 p. 658-667.

Peroxide Oral Care Products, Heath Canada, http://www.hc-sc.gc.ca/dhp-mps/prodpharma/applic-demande/guide-ld/label-etiquet-pharm/perox-eng.php, Accessed on Oct. 23, 2007.

Rees, Terry D. et al., Oral Ulcerations with Use of Hydrogen Peroxide, Journal of Periodontology, vol. 57 (11), Nov. 1986, p. 689-692.

Shetty, Kishore, Hydrogen Peroxide Burn of the Oral Mucosa, The Annals of Pharmacotherapy, vol. 40, No. 2, Feb. 2006, p. 351.

Tooth Whiteners Containing Hydrogen Peroxide, Green Facts, http://copublications.greenfacts.org, Accessed on Nov. 1, 2007.

Tredwin, J. et al., Hydrogen peroxide tooth-whitening (bleaching) . . . effects and safety issues., Dental Journal, vol. 200, No. 7, Apr. 8, 2006, p. 371-376.

Walsh, LJ., Safety issues relating to the use of hydrogen peroxide in dentistry., Australian Dental Journal, vol. 45(4), Dec. 2000, p. 257.

White, J.D. et al., The Dental Cosmos: A Monthly Record of Dental Science, vol. 35, Philadelphia, 1893, p. 330-332.

Melkonyan, Robert, Facts About Safety and Effectiveness of Teeth Whitening Products, 2008, p. 1-2.

Nafer, Barb, Hydrogen Peroxide for Teeth Bleaching, Jun. 12, 2010, http://www.livestrong.com/article/147103-hydrogen-peroxide-teeth-bleaching/.

Strassler, Howard E., Continuing Education, Dec. 8, 2006, p. 1-11.

Tooth Whitening/Bleaching: Treatment Considerations for Dentists and Their Patients, ADA Council on Scientific Affairs, Sep. 2009, p. 1-9.

Tooth Bleaching, Wikipedia The Free Encyclopedia Jun. 23, 2013, http://en.wikipedia.org/wiki/Tooth_bleaching.

* cited by examiner

FIGURE 7
SUSTENANCE OF BICARBONATE ION

ORAL HYGIENE COMPOSITION AND APPARATUS AND METHOD

FIELD OF INVENTION

The present invention relates to the field of portable oral care preparations, including cosmetic teeth whitening and breath freshening preparations, as well as preventive and remedial chemotherapeutic preparations and treatments for common human oral problems, including periodontal diseases and halitosis. It also relates to apparatus for delivering such preparations

BACKGROUND OF INVENTION

The development of tooth whitening techniques has been taking place for well over 100 years. It is well known that the teeth can be effectively bleached by the use of hydrogen peroxide as the bleaching agent, and it is proven that, in general, tooth-whitening preparations having higher concentrations of bleach are more effective in whitening the teeth than those of lesser concentration. Thus, increasing concentrations of the bleaching agent in the bleaching gives rise to a more rapid bleaching action. The problem with the higher concentrations of bleaching solutions is that they have been proven to be painful to endure, and injurious to oral tissue, including blistering and severe discomfort to the gingiva (gum) and other soft tissue present in the oral cavity. It is well documented that oral rinse preparations of hydrogen peroxide having concentrations greater than 6% are dangerous for use in the human oral cavity, since exposure of the oral soft tissues for times on the order of seconds, has been demonstrated to cause immediate injury to the gingival and soft tissue of the human oral cavity. In general, it has been well established that the greater the concentration of hydrogen peroxide oral rinse, the faster and more severe this burning affect to the gingival and soft tissue after exposure to these oral rinse solutions. This safety issue has been the barrier and challenge to the development of tooth whitening techniques.

Tooth whitening using aqueous, or ethereal solutions of extremely high concentration of hydrogen peroxide (25%-35%) are well established as the fastest and most permanent methods available, today. These treatments require professional guidance and care, and are typically carried out in the dental office by a highly trained dental professional. This method is referred to as vital bleaching, and is tedious, and dangerous if carried out without professional application. Vital bleaching requires physical protection of the gums from exposure to the highly concentrated bleach solution (gingival dam). The dental professional custom fits a plastic damming structure around the gingiva, also places a retractor inside the lips and then lifts the lips away from the front surfaces of the teeth to keep the inside of the lips and other oral soft tissue from contact with the powerful bleaching solution. These techniques are necessary to avoid the inevitable and immediate sharp pain and burning sensation that would take place immediately without such, and also to minimize damage to the gingiva and oral soft tissue due to the aggressive burning of the tissue from the concentrated hydrogen peroxide bleach. This method has been shown to be the most effective tooth whitening method available, but is limited in its usefulness, since it must be performed by the dental professional, and requires 1-6 visits to the dental office and takes at least an hour to perform each visit, and cost ranges between $500 to $3,000 USD; rather expensive and time consuming for the average person. A popular in-clinic vital bleaching method uses heat or UV light to activate the peroxide, bleach in situ and is named Zoom Whitening.

A strong desire for do-it-yourself tooth whitening methods and products exists, as evidenced by the current market popularity of many do-it-yourself products commercially available. One such product is comprised of a viscous bleaching gel contained in a professional or non-professionally fitted plastic tray, designed to provide a reservoir for the bleach as a viscous gel, and to encase the upper or lower teeth where whitening is desired. The method has the bleach in a tray to minimize exposure to the sensitive tissue. The gel form of the hydrogen peroxide bleach has the advantage in minimizing discomfort to the user, in that the exposure of the bleach to the enamel is slow due to the gel's high viscosity, and even if a leak occurs and the bleach touches the sensitive tissue, the concentration of the bleach is much lower than those employed by the vital bleaching technique. Some of the popular tray method products include Den Mat Night White, and Opalescence (3.5-8% bleach [10%-25% urea hydrogen peroxide, respectively]). The method has the user apply the tray daily for periods ranging from 20 min to 12 hours for at least 10-14 sequential days. This method has the advantage to the vital bleaching method because it can be done in the privacy of one's home and achieves reasonably good results. It uses gelled forms of bleaching solutions that are quite viscous, and more concentrated that what is available OTC for safe oral rinse application (1.5%-3% hydrogen peroxide), but much less concentrated than the vital bleaching method (25%-35% hydrogen peroxide). Typically, the concentrations of peroxide bleach in these tray method gels are on the order of 3.5% peroxide to about 8% peroxide, where urea is used as a stabilizing agent. A 10%-25% urea hydrogen peroxide gel provides for 3.5%-10% hydrogen peroxide activity, respectively. The tray method suffers because it is uncomfortable, time consuming and messy to use. Since the tray is fashioned to have the gel exposed to the front surfaces of the teeth, it only results in the bleaching of the front portions of the teeth encased in the tray. The method does not bleach teeth that are not encased by the tray, nor does it bleach the back and side areas of such teeth. In summary, the tray method suffers from the requirements that: (a) it must be performed multiple times (10-60); (b) it must stay on for an extended period of time each use (20 min-12 hr); (c) it is accompanied with some discomfort due to poor fitting trays, and dehydration of the teeth, and is messy to use, and; (d) in most cases still requires an initial visit to the dental professional to create the tray and provide instructions, and; is costly, the price ranging from 300-600 USD, and; (e) it does not provide the ability to bleach the inside portions, and hard to reach side portions of the teeth.

A similar technology is the "strip matrix" in which the hydrogen peroxide bleach solution of 6% (Crest Whitestrips, Procter and Gamble) or 14% (Crest Whitestrips Supreme, Procter and Gamble) is a thin layer on a plastic strip that is applied directly to the surface of the teeth. Bleaching of the front portions of the teeth takes place slowly over time by having the hydrogen peroxide slowly leak out of the strip matrix directly onto the surface of these teeth. The strip matrix minimizes exposure of the bleach to the sensitive tissue, since it does not touch the soft tissue and gingival tissue. Typically, the treatment requires the user to keep the strip on the teeth for about 20 minutes, repeating this procedure once a day for at least 5-14 days to see significant results. The technique has been reported as less uncomfortable than the "tray method", with similar tooth whitening results. Significant disadvantages are the length of time needed to get the desired whitening, the requirement for multiple uses, and the need for privacy during usage, since the wearing the strips in public has social disadvantages and are, in general, inconvenient, and also the inability to bleach the areas in between the teeth, and the back portions of the teeth.

Tooth whitening toothpaste compositions are also commercially available, but most of these use abrasion rather than bleaching agents for the tooth whitening action. Those tooth whitening toothpaste preparations that do include bleaching agents have the bleach at very low concentrations. The effectiveness of tooth whitening toothpaste products are, at best, none to moderate.

Oral rinse solutions have been commercially sold as tooth whitening and breath freshening mouthwash products (one current commercial example is Crest Tooth Whitening Oral Rinse), and similar solutions have been utilized as a breath freshening and tooth whitening spray (U.S. Pat. No. 5,611, 690). These oral rinse methods are limited in the amount of the bleach that can be utilized in the bleaching solution, which in these cases are also breath freshening solutions, since oral rinses having greater than 3% are known to be dangerous to the user if left in the mouth for much longer than 15 seconds. In Europe and Canada, it is illegal to dispense tooth whitener or breath freshening products having concentrations of hydrogen peroxide greater than 1.5%, and 3% respectively. Thus, any tooth whitening effect of these types of oral rinse solutions is minimal, at best. Effective tooth bleaching action for these types of products would, in concept, require much longer exposure times than is practically possible for these lower concentrated solutions of bleach. Since the decomposition of peroxide in the oral cavity would most likely occur before any appreciable tooth whitening, and the corresponding pain and possibly injury to the user most likely would be a result of these long durations of exposure, these oral rinse tooth whitening methods are severely hampered.

One method to overcome the extremely long duration required to achieve any appreciable tooth whitening of oral rinse breath freshening and, hypothetically, tooth-whitening solutions, is to increase the frequency of usage. Such a method was taught by Summers et al. in U.S. Pat. No. 5,611, 690, where he teaches a spray method for application of these types of oral rinse solutions many times throughout the day (over 7 treatments a day). Any tooth whitening efficacy of this spray method is severely hampered due to the low strengths of hydrogen peroxide, and due to the inconvenience of having to use it many times throughout the day in order to achieve any appreciable tooth whitening. The tooth whitening results described by his teachings are not reported in a manner consistent with scientific standards, but rather anecdotally, and based on the formulas tested, would be expected to be moderate, at best since the example provided has less than 3% [H2O2]. Another important drawback to the teachings of Summers et al. is the danger to the user as a result of misdirected spray. It is highly probable that the spray mist containing the peroxide and breath freshener, according to his teachings using the spray apparatus detailed in his invention, may easily be misdirected to non-targeted areas such as facial tissue, and eyes, and clothes. It is well known for solutions of hydrogen peroxide of tooth bleaching strength (1.5%-40%) that contact with the lips and skin will be painful and injurious to the user due to the immediate burning that takes place on such tissues. Contact with the eyes with the spray mist comprised of hydrogen peroxide causes serious burning, sometimes irreversible and even blindness can occur. Irreversible damage to clothing fabric is imminent upon contact with hydrogen peroxide solutions (or spray mist forms of the solutions)—even at lower concentrations of hydrogen peroxide provided, by example in U.S. Pat. No. 5,611,690.

The rationale for formulating these breath-freshening bleaching solutions provided by example in the spray taught by Summers et al. was, most likely, based on the understanding of the tooth whitening and oral hygiene art before the present invention. That is, since no evidence had been provided by the teachings of the tooth-whitening and oral care art to suggest otherwise, hydrogen peroxide solutions having concentrations greater than 3% were considered as dangerous agents for use as oral rinses in the human mouth and, therefore, were considered dangerous for use as an oral spray. As a direct result of this wisdom, the obvious concentration of hydrogen peroxide for employment in the teachings of Summers et al. was those of accepted oral compatibility as oral rinse solutions, i.e., less than 3% hydrogen peroxide.

The need exists for a tooth whitener that is convenient, safe and effective, without the disadvantages of the prior methods, which are the following: (a) the high cost and inconvenience of professional application of highly concentrated solutions of bleaching agent (vital bleaching method) to achieve the optimal tooth whitening results; (b) the high probability of serious injury resulting from non-professional application of the higher concentrations of hydrogen peroxide, including the vital bleaching method and spray method of Summers et al.; (c) the inconvenience that the user must endure with the spray method taught by Summers et al. due to the high frequency of usage required for, at best, poor to moderate tooth whitening results; (d) the long duration of contact with the bleaching agent required by the tray and strip methods and the corresponding inconvenience engendered; (e) the increased discomfort effected to gingiva and soft tissue of the oral cavity by the vital bleaching, tray and strip methods; (f) the inconvenience of multiple uses or socially unacceptable paraphernalia such as a tray or strip, (g) the lack of bleaching activity on the non-front surfaces of the teeth.

Periodontal diseases, including gingivitis, are a major contributor to ill health in the United States and worldwide. Periodontal diseases if left unchecked can cause the loss of teeth, and most likely will lead to an array of systemic diseases and maladies, and many of these diseases, unfortunately, will ultimately result in serious debilitation or in many cases, death. Preventive treatments for periodontal diseases include antibacterial topical solutions or oral rinses, in addition to a well-practiced regimen of good oral hygiene comprised of tooth brushing and flossing. Remedial treatments for periodontal diseases include scaling and root-planning procedures carried out in the clinic by the periodontist, and in severe cases, removal of the diseased tooth body. Another well-accepted method of prevention and remedial treatment for gingivitis (early stages of periodontal disease) is that described by Dr. Keyes (known as the Keyes technique), where a mixture of baking soda and hydrogen peroxide are applied directly to the teeth (hard tissue) and gums (soft tissue), usually by a tooth brushing methodology. The results obtained from such method for the prevention and remediation of early stage periodontal disease is moderate to significant, however, this Keys methodology suffers from being rather inconvenient and fowl tasting.

The need exists for a convenient and effective means to safely and effectively prevent and remediate periodontal diseases.

Halitosis (oral malodor) is another common oral ailment affecting millions of people worldwide. The main cause of halitosis is the presence of sulfides and amino-based compounds generated as metabolic products of certain anaerobic oral bacteria. It is the sustained ill-growth of certain oral bacteria that thrive in the pockets of the gingival that give rise to the halitosis problem. Most of these bacterial species are also important for the incidence of gingivitis and periodontal diseases. Thus, controlling the ill-growth of certain anaerobic bacteria that thrive in the pockets of the gingiva where oxygen supplies are minimal is important, since such control would most likely result in an increase in health for the gingiva and a less odiferous oral cavity. This benefits the user chemotherapeutically by aiding the prevention of serious systemic and oral ailments, and aesthetically by providing the user with a confident and healthy smile. The reduction of such bacteria and bacterial chemical metabolic by-products such as odiferously unpleasant oral sulfides and amines, have been achieved to some degree by employing a regiment of daily usage of oral rinses including such drugs as chlorhexidine, and/or lesser active agents such as mineral spirits, zinc or copper salts. The Keyes technique has also been employed to address the reduction in halitosis causing agents. All of these techniques suffer from the inconvenience of the requirement that they are used in the home or office, which limits the number of times the user may employ these treatments throughout the day. It is the frequency of usage that gives rise to the effectiveness in many of these agents and techniques, so lack of usage gives rise to lack of significant results.

The need exists for an oral preparation that is not professionally administered and that is convenient to use, and is safe and effective in reduction of oral anaerobic bacteria and the chemical agents of halitosis.

DETAILED DESCRIPTION OF INVENTION

All percentages of concentrations given herein are by weight.

The present invention solves salient problems of prior technologies by providing a novel tooth whitening method and apparatus that is easy, discrete and convenient to use, and is quick acting to achieve tooth whitening results that are typically obtained from methods utilizing the professional office; and markedly better than any out-of-office treatment offered in today's marketplace. Such unprecedented efficacy derived from an out-of-office technique is afforded by the present invention by providing for a safe method and apparatus for applying an increased concentration of hydrogen peroxide directly to the surfaces of the teeth to be bleached; while being completely devoid of the safety concerns which hampered the prior art. Specifically, the present invention, in its essential and preferred embodiment, provides for an aerosol containing hydrogen peroxide of appreciable and effective concentrations (5%-40%), to be sprayed directly onto the teeth without the anticipated sensitivity to the gums and oral tissues. In addition, the present invention teaches a spray method and apparatus therefore that avoids the potential harmful effects of having the bleaching solution contact the eyes, lips, facial tissue, and other sensitive human tissue, and garments due to misdirected spray. Also, the present invention overcomes the need for many applications, since the present invention teaches compositions and methods where the user employs the spray process once every third day, or once a day, depending on the strength of the treatment. Also, the inconvenience of the prior art in connection with long duration times of treatment using apparatus that requires privacy, in particular the tray and strip methods, are overcome by the present invention. The present invention employs a convenient spray method, which can be practiced without the need to hide or experience embarrassment and is effective in less than 2 minutes. The need for convenient oral preparations to aid in the prevention and remediation of gingivitis, periodontal diseases, and halitosis is met by the present invention by incorporation of the alternatives; that is by incorporation of the plaque removal and antiplaque compositions of Arnold as described in U.S. Pat. Nos. 6,086,854, 5,965,110, and 5,804,165 (hereafter "Arnold") as pre and post tooth whitening treatments. The entire content of each of U.S. Pat. Nos. 6,086,854, 5,965,110, and 5,804,165 is incorporated herein by reference.

The present invention, in a primary embodiment, teaches a safe and effective tooth bleaching spray composition, comprised of certain aqueous solutions of concentrated hydrogen peroxide. The terms "whitening" and "bleaching" are used synonymously herein. The concentration of the hydrogen peroxide delivered as an aerosol spray, taught by the present invention, is between 5% and 40%, preferably between 6% and 37%, most preferably between 9% and 35%. These hydrogen peroxide solutions may have other additives, including flavorings and surfactants. The preferred dosage for a single aerosol spray event is an aliquot of from about 5 mg to 1000 mg, the more preferred aliquot is from about 15 mg to 750 mg, and most preferred from about 35 mg to 225 mg. It has been observed that the smaller the droplet size in the aerosol spray, the lesser is the sensitivity. The device to deliver the aerosol spray is made from hydrogen peroxide compatible material, such as polyethylene, polypropylene, or glass, or other materials known safe to store hydrogen peroxide, and are adaptations of spray devices, common to modern cosmetology and oral spray technology, or to compressed gas aerosol spray technology. The adaptations of the spray devices for application in the present invention include a specially configured mouthpiece, where the lips surround the mouthpiece and thus inhibit or block the spray solution from exiting the targeted dental areas while directing it to the target areas. Descriptions of embodiments of the spray devices of the present invention are provided below and shown in the figures. It is important to note that the mouthpiece embodiments described by the illustrations of FIGS. 1-6 are meant to be representative examples. That is, other mouthpiece designs may be included within the scope of the present invention, as long as they serve the purpose to: (1) protect the lips, facial tissue, nose mucosal tissue, eye tissue, other external tissues, and garments from the peroxide containing aerosol; (2) aid in the focus of the spray to the surfaces of the enamel, and; (3) inhibit, to some degree, the aerosol bleaching mixture from direct contact with inner oral surfaces of the lips. Also, the mouthpiece embodiments are shown in forms that can be applied to known dispensing containers as well as for especially made dispensing containers. These preferred spray devices are important to the present invention by inhibiting the spray from escaping from the mouthpiece, since spray forms of hydrogen peroxide solutions having concentrations between 5% and 40%, can be damaging to the eyes, and cause an immediate discomfort and burning sensation to the lips and facial skin tissues, and since they also serve to eliminate the potential problem of the spray from reaching the garments the user is wearing, where exposure to hydrogen peroxide would ruin the garment. The proper use of this preferred embodiment is to have the lips of the user wrap around the mouthpiece device, thus inhibiting the spray from interacting with tissue and material external to the inside of the oral cavity. Such an employ also facilitates the user comfort and safety aspects of the present invention by minimizing the exposure to the non-keratinized soft tissue, which includes the inner lips and inner-oral tissues, including the tongue. It also serves to help direct and focus the spray particles onto the target surfaces of the hard tissue of the enamel. The spray may be a pump aerosol spray, or an aerosol spray form having the hydrogen peroxide solution propelled by compressed inert gas, usually butane gas, and as such having a corresponding aerosol container suitable to such pressures and such a delivery system. Such gas-propelled or hand actuated pump aerosol spray delivery systems are commonplace in today's consumer market.

The apparatus of the invention in one embodiment is a mouthpiece attachment to a spray canister, the attachment being configured to attach to the spray canister to allow the canister contents to be sprayed into the mouthpiece attachment and to allow the spray to be sprayed into the user's mouth, directed to the teeth while inhibiting any escape of the spray.

One embodiment of the attachment is shown in FIGS. 1A-1D showing a spray attachment 10. The spray attachment 10 has a nozzle adapter end 12 and a spray control end 14 also referred to as a mouthpiece portion, which is configured as a circular walls 16a, 16b, 16c defining a progressively enlarging interior volume 18. The circular walls start at a proximate end with a smaller cylindrical portion 16a, then to a frustum portion 16b and then to a final cylindrical portion 16c at a distal end. As will be seen this configuration helps with the sealing effect when it is placed in a user's mouth since the lips can surround the smaller portions 16a and 16b and allow the larger portion 16c to be proximate the teeth in order to direct the spray onto the teeth. A spray entry opening 20 at the proximate end extends through the nozzle adapter end 12 into the interior area. The spray attachment 10 is fitted to a spray bottle 22 that has a spray nozzle 24. The nozzle adapter end 12 is configured in this embodiment as an insert tube 26 and a transition frustum 28 that can be inserted into the spray nozzle 24 and sealed to ensure that the full volume of spray is ejected as a fine aerosol mist from the spray bottle 22 when it is operated, directing the aerosol spray exiting the spray nozzle 24 through the spray attachment 10 from which it is expelled at the opening of the distal end as an aerosol spray onto the target area.

Figure 1A:
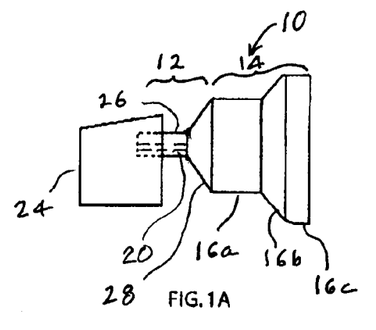
FIGS. 1A, 1B, 1C and 1D are views of a mouthpiece.
Figure 1B:
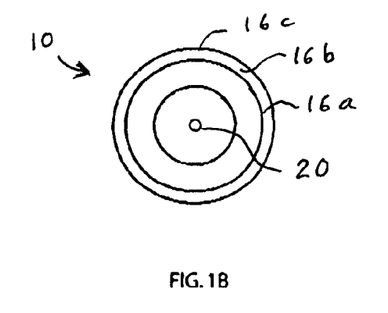
Figure 1C:
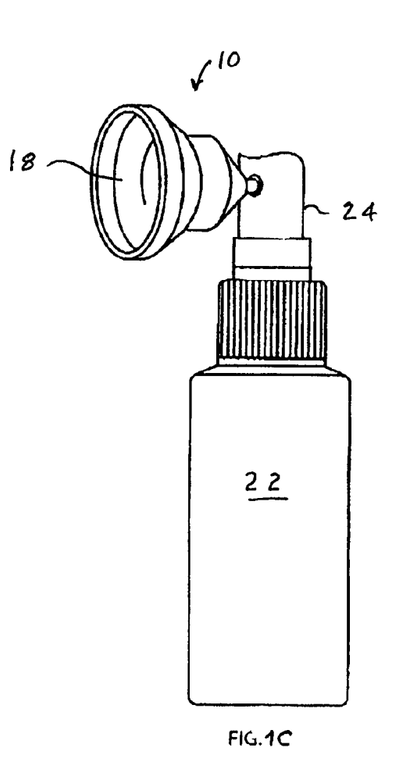
Figure 1D:
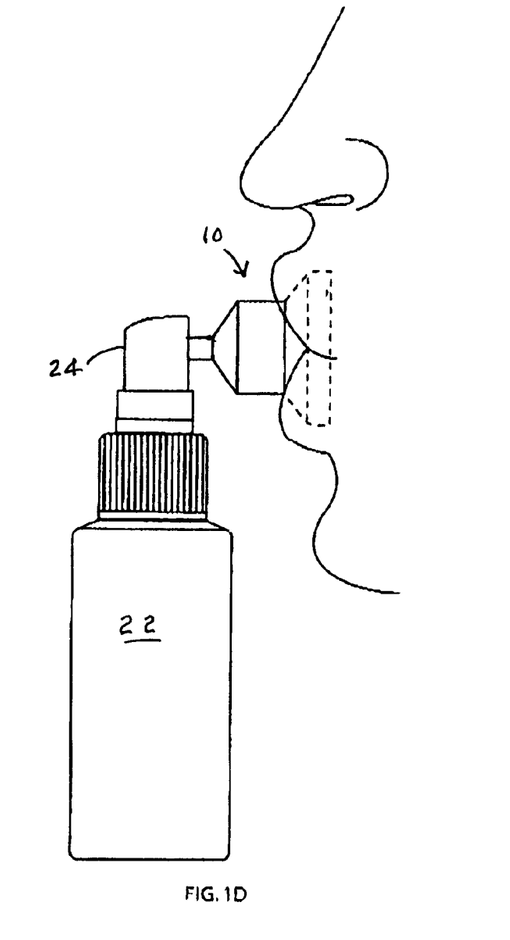

FIG. 1D shows how the spray attachment 10 is inserted into the user's mouth. It will be surrounded by the user's lips in a sealing manner on the exterior of the mouthpiece portion 14 so that no spray can escape into contact with the lips, or outside the user's mouth into contact with the face, nose, eyes or clothes. Because of the configuration of the mouthpiece portion 14, the user's lips can close on the cylindrical portion 16a, with the frustum portion 16b on the interior of the lips and the cylindrical portion 16c directing the aerosol spray toward the teeth.

In use, with a tooth whitening solution in the spray bottle 22 the spray control end 14 is inserted into the oral cavity is shown in FIG. 1D, where the lips surround and encase the exterior of the mouthpiece portion 14, thereby inhibiting the ejection of any misdirected solution and keeping it away from the eyes, nose, facial tissue and clothes. Proper usage has the user hold the apparatus placing the distal end opening in close proximity to the teeth in a selected starting position, typically at one side of the mouth at a series of teeth, although starting at the front is also available, pump the spray nozzle 24 once, then sequentially move it laterally and repeating the sequential spray steps 2-6 times until all the teeth have been sprayed with the whitening aerosol spray solution. The diameter of the exit of cylinder 16c can range from about ¾ in. to about 1½ in, 1¼ in being preferred so as to fit a wide range of users.

FIGS. 2A-2D shows another configuration of a spray attachment 30 like the one shown in FIGS. 1A-1D but with a simpler configuration of the spray attachment 30. The spray attachment 30 has a nozzle adapter end 32 and a spray control end 34 also referred to as a mouthpiece portion, which is configured as a cylinder 36 so that the interior space has an axially constant volume 38. This configuration allows a sealing effect when it is placed in a user's mouth. An opening 40 extends through the nozzle adapter end 32 into the interior volume 38. The spray attachment 30 is fitted to a spray bottle 42 that has a spray nozzle 44. The nozzle adapter end 32 is configured in this embodiment as an insert tube 46 and a transition frustum 48 that can be inserted into the spray nozzle 44 and sealed to ensure that the full volume of spray is ejected as a fine aerosol mist from the spray bottle 42 when t is operated, directing the spray exiting the spray nozzle 42 through the spray attachment 30 from which the spray is expelled as an aerosol spray.

Figure 2A:
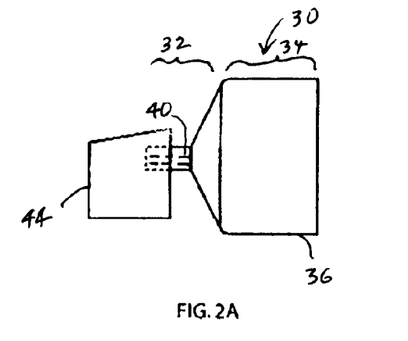
FIGS. 2A, 2B, 2C and 2D are views of another mouthpiece.
Figure 2B:
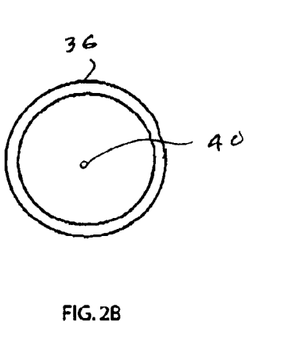
Figure 2C:
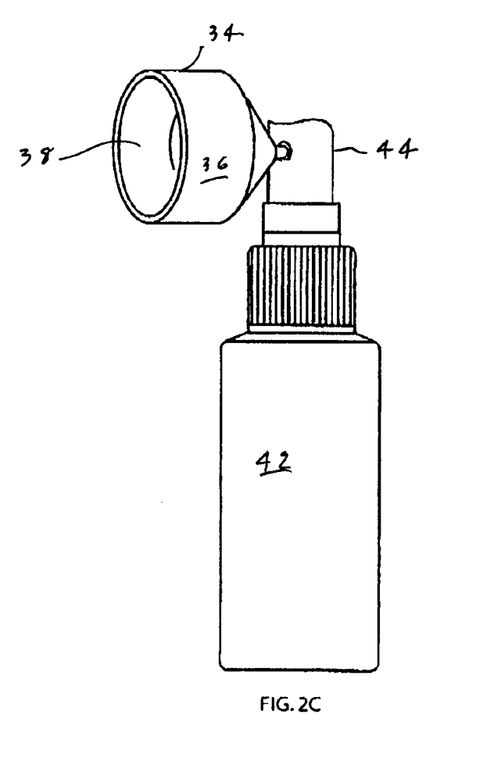
Figure 2D:
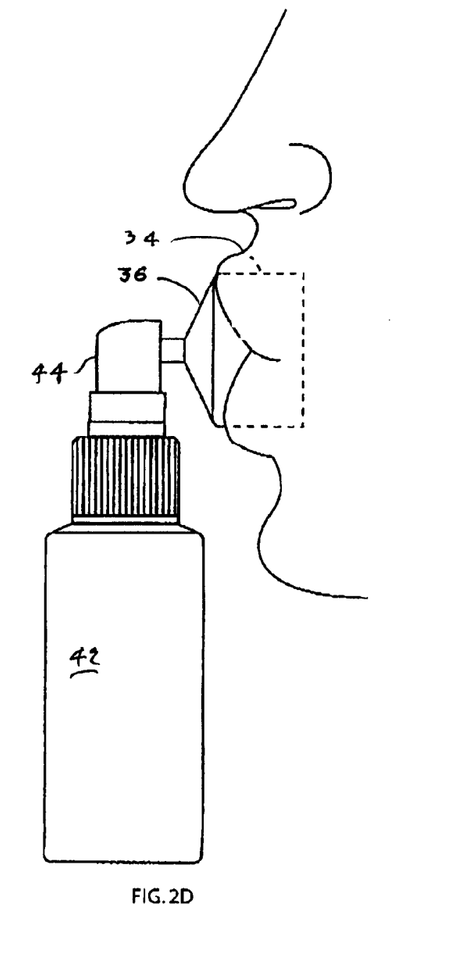

FIG. 2D shows a proper fit for the cylindrically shaped spray control end 34 into the oral cavity, where the user's lips, surround the spray control end 34, encasing its outer surface forming an substantial seal, thereby inhibiting the ejection of any misdirected whitening solution and keeping it away from the eyes, nose, facial tissue and clothes. Proper usage has the user hold the apparatus, pump the spray nozzle 24 once, then move the unit laterally starting from one side of the mouth, and repeating the spray process 2-6 times until all the teeth have been saturated with the whitening aerosol spray solution.

Figure 3A:
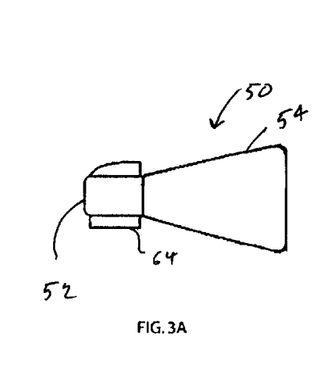
FIGS. 3A, 3B, 3C, 3D, and 3E are views of another mouthpiece.
Figure 3B:
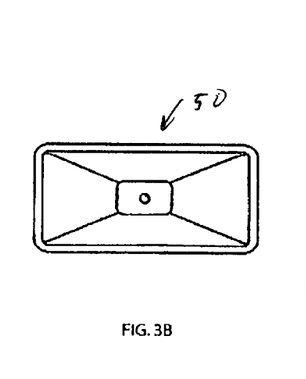
Figure 3C:
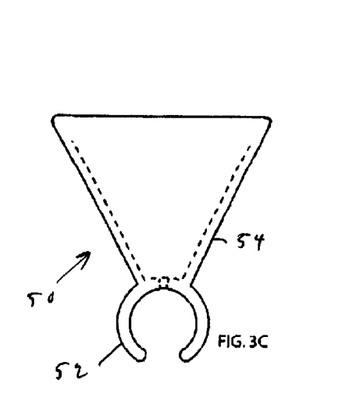
Figure 3D:
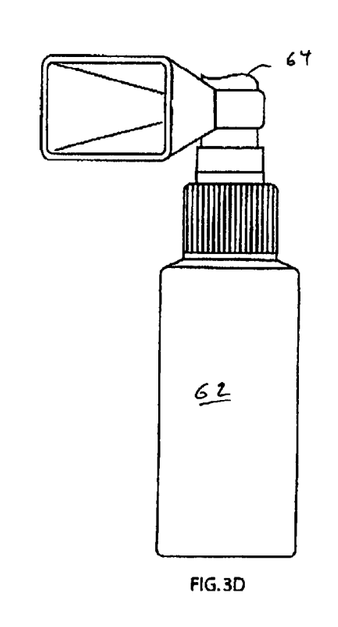
Figure 3E:
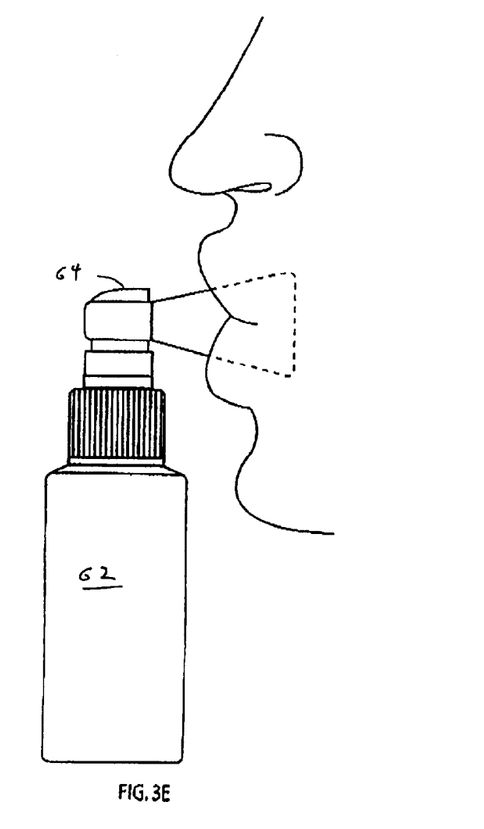

Another embodiment of the attachment is shown in FIGS. 3A-3E showing a spray attachment 50. The spray attachment 50 has a nozzle adapter end 52 and a spray control end 54 also referred to as a mouthpiece portion which is configured as an expanding rectangular cross-section defining a progressively enlarging interior volume 58. An opening 60 extends through the nozzle adapter end 52 into the interior volume 58. The nozzle adapter end 52 has a clip-on configuration, having curved legs 56a and 56b that are sufficiently flexible to grip the spray nozzle 64 on the spray bottle 62, so that the opening 60 is aligned with the orifice of the spray nozzle 64, thereby maintaining the integrity of the spray directed into the volume 58. This embodiment can also be made so that the spray attachment 50 is integral with the spray nozzle 64, in which case the legs 56a and 56b would form a closed circle. FIG. 3E shows a proper fit into the oral cavity where the user's lips, surround the mouthpiece portion 54, encasing the outer surface, forming an airtight seal, thereby inhibiting the ejection of any misdirected whitening solution and keeping it away from the eyes, nose, facial tissue and clothes. Proper usage has the user hold the apparatus, pump the spray nozzle head 12, once, then move the hand-held spray bottle 62, laterally starting from one side of the mouth, and repeating the spray process 2-6 times until all the teeth have been saturated with the whitening aerosol spray.

Figure 4:
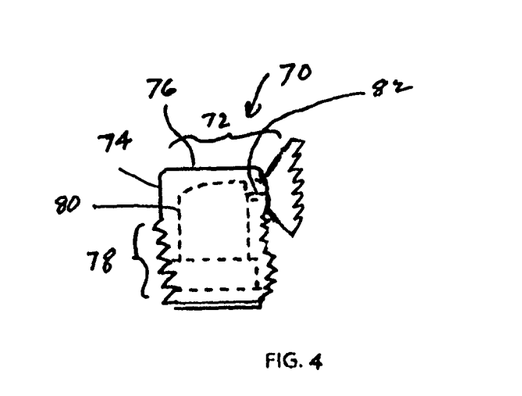
FIG. 4 is a partial view of a mouthpiece fitted to a spray device.

Another embodiment of the attachment is shown in FIG. 4. In this embodiment the attachment 70 has a nozzle adapter end 72 which has a soft plastic cover member 74 which is sufficiently flexible that when depressed from the top as at 76, it will collapse along a portion shown at 78 below the orifice of the spray nozzle 80. This will maintain an opening 82 in the nozzle adapter end 72 aligned with the exit orifice of the spray nozzle 80. The mouthpiece end of this embodiment can have any desired configuration.

Figure 5A:
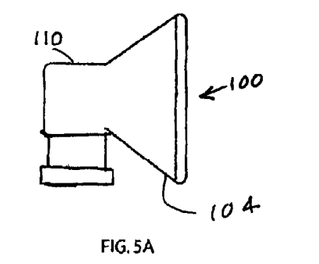
FIGS. 5A, 5B, 5C, 5D, and 5E are views of another mouthpiece.
Figure 5B:
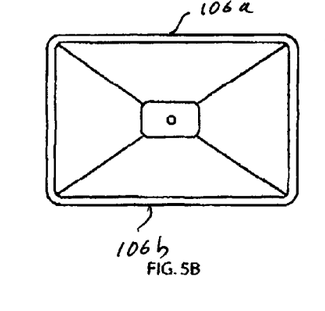
Figure 5C:
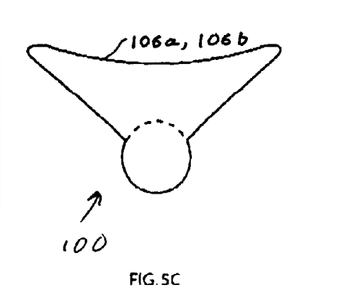
Figure 5D:
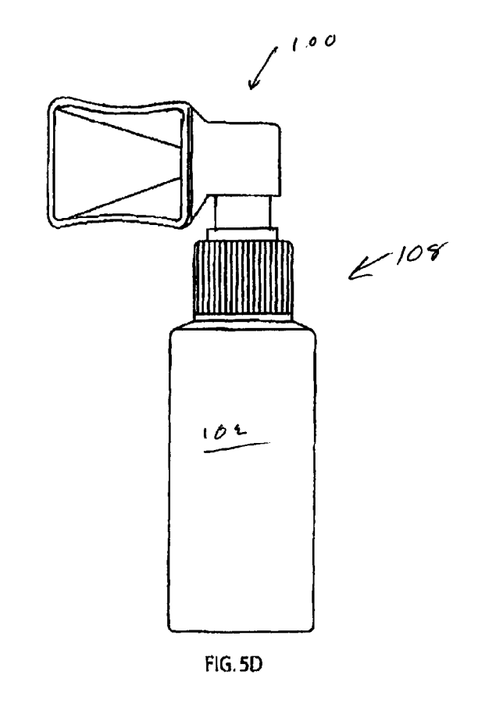
Figure 5E:
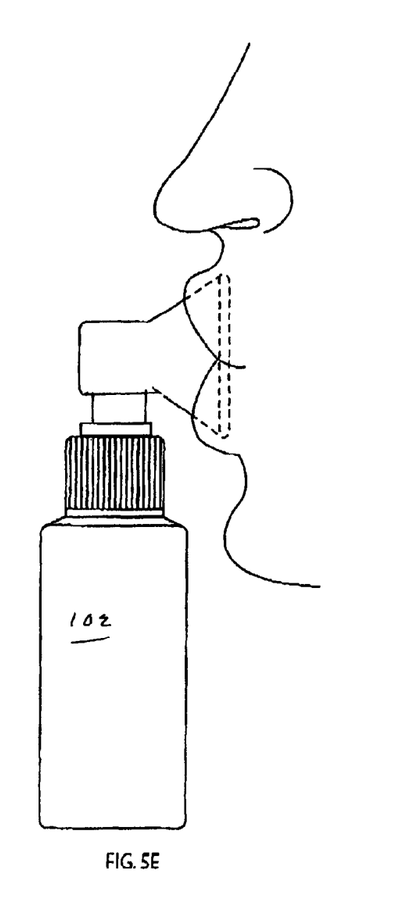

Another embodiment is shown in FIGS. 5A-5E showing an integral spray nozzle 100 on a spray bottle 102. The shape of the mouthpiece end can be selected as desired, including any of the configurations described herein as well as other configurations that are made to direct the whitening aerosol spray to the user's teeth and at the same time providing a seal to the user's lips to inhibit escape of any of the spray. This spray nozzle 100 is different from those depicted in the previous description because it is assembled as an integral spray nozzle head 110 with a spray bottle 102, including the channel required to eject the whitening solution as a fine aerosol spray; although it could also be supplied to be fitted to a pre-existing spray bottle as in the previous examples. In this embodiment the mouthpiece 104 is configured as an expanding rectangular cross-section ending in concave upper and lower edges 106a and 106b adapted to follow the general curvature of the upper and lower dental areas of a typical human oral cavity. A complete hand-held spray tooth whitening device 108, is illustrated in FIG. 5D, where the spray nozzle head 100 is assembled as an integral part of typical atomizer bottle 102. A cylindrical container having a volume of 2 ml is depicted as the atomizer pump reservoir. An illustration of a proper fit for the spray control end 104 is shown in FIG. 5E, where the user's lips surround the mouthpiece portion 104, encasing its outer surface, forming an airtight seal, thereby inhibiting the ejection of any misdirected whitening solution and keeping such away from the eyes, nose, facial tissue and clothes. The curved shape of the edges 106a and 106b keep the exit of the mouthpiece portion generally equally spaced from the user's teeth by reason of the curvature. Proper usage has the user hold the apparatus pump the spray nozzle head once, then move the hand-held spray unit laterally starting from one side of the mouth, and repeating the spray process 2-6 times until all the teeth have been saturated with the whitening aerosol spray.

Another embodiment of the spray apparatus is shown in FIGS. 6A-6D showing a typical bulb pump 120 attached to a bottle 122. In this configuration any selected shape for the spray control end can be used; the one illustrated being the one shown in FIGS. 2A-2D for illustration purposes. Proper usage has the user hold the apparatus, pump the atomizer bulb 124 once to 10 times, then move it laterally starting from one side of the mouth, and repeating the spray process 2-6 times until all the teeth have been saturated with the whitening aerosol spray.

The present invention includes the discovery that, as an aerosol spray (the term aerosol referrers to any liquid suspended as fine droplets in gaseous phase), application of certain concentrated hydrogen peroxide aqueous solutions to be devoid of any of the anticipated ill effects to the keratinized soft tissue of the oral cavity (gums), such as chronic sensitivity, chronic burning sensation. It has also been discovered that application, in accord with the present invention, of these highly concentrated solutions of hydrogen peroxide as aerosols, in comparison to the results obtained by practicing the teachings of the prior art, results in significantly reduced sensitivity to the pallet and tongue and, in general are devoid of serious damage of the oral inner membranes including inner lips and oral mucosa. It is noteworthy that such ill effects are the well-established toxicological properties for mouth rinses and oral preparations comprised of solutions of hydrogen peroxide having the strengths taught by the present invention as safe for human use. A clinical study was undertaken to investigate the difference between the liquid mouth rinse preparations of the prior art in direct comparison to their aerosol counterparts of the present invention. The results are described in Table 1.

In the use of the hydrogen peroxide aerosol application, after application the resulting saliva mixture should be expectorated (the terms expelled and expectorated are synonymous)

TABLE 1

COMPARATIVE SINGLE USE MEASUREMENT OF SOFT TISSUE SENSITIVITY
DIRECT COMPARISON OF A 12.5% HYDROGEN PEROXIDE AQUEOUS ORAL RINSE SOLUTION TO ITS SPRAY AEROSOL COUNTERPART

| SUBJECT | 12.5% RINSE | 12.5% SPRAY | CHANGE |
|---|---|---|---|
| 1 | 5 | 1 | −4 |
| 2 | 5 | 2 | −3 |
| 3 | 5 | 1 | −4 |
| 4 | 5 | 1 | −4 |
| 5 | 5 | 1 | −4 |
| 6 | 5 | 2 | −3 |
| 7 | 5 | 2 | −3 |
| 8 | 5 | 1 | −4 |
| 9 | 5 | 1 | −4 |
| 10 | 5 | 1 | −4 |
| 11 | 5 | 2 | −3 |

SCORING:
1 NONE
2 MILD IRRITATION
3 MODERATE SENSITIVITY
4 HIGH SENSITIVITY, EXPECTORATION REQUIRED BEFORE TWO MINUTES
5 CHRONIC - EXPECTORATION REQUIRED BEFORE 1 MINUTE
6 CHRONIC - EXPECTORATION WITHIN SECONDS (LEGALLY NOT ADVISED, HARMFUL, IMMEDIATE SERIOUS DAMAGE TO ORAL TISSUE

These data demonstrate conclusively that the anticipated unsafe and ill-effects of the oral rinse preparations of the present invention of the soft tissue, is due to the higher concentrations of hydrogen peroxide (12.5% in the study of Table 1).

A direct comparison of the highly concentrated 35% hydrogen peroxide spray aerosol mixture to the corresponding oral rinse solution of similar strength was also carried out, and the results are displayed in Table 2.

TABLE 2

SINGLE USE MEASUREMENT OF SOFT TISSUE SENSITIVITY
DIRECT COMPARISON OF A 35% HYDROGEN PEROXIDE AQUEOUS ORAL RINSE SOLUTION TO ITS SPRAY AEROSOL COUNTERPART, ONE 2-MINUTE TREATMENT

| SUBJECT | 35% RINSE | 35% SPRAY | CHANGE |
|---|---|---|---|
| 1 | 6 | 2 | −4 |
| 2 | 6 | 2 | −4 |
| 3 | 6 | 2 | −4 |
| 4 | 6 | 1 | −5 |
| 5 | 6 | 2 | −4 |
| 6 | 6 | 2 | −4 |
| 7 | 6 | 2 | −4 |
| 8 | 6 | 1 | −5 |
| 9 | 6 | 3 | −3 |
| 10 | 6 | 2 | −4 |

SCORING:
1 NONE
2 MILD IRRITATION
3 MODERATE SENSITIVITY
4 HIGH SENSITIVITY, EXPECTORATION REQUIRED BEFORE TWO MINUTES
5 CHRONIC - EXPECTORATION REQUIRED BEFORE 1 MINUTE
6 CHRONIC - EXPECTORATION WITHIN SECONDS (LEGALLY NOT ADVISED, HARMFUL, IMMEDIATE SERIOUS DAMAGE TO ORAL TISSUE

As evidenced by the results displayed in Table 1 and Table 2, a heretofore-deemed unsafe and harmful solution of concentrated hydrogen peroxide, is completely safe for use in the oral cavity when applied as a spray aerosol mixture of the present invention. In particular, when sprayed on the subjects' teeth, including incidental contact with the gingiva and other soft tissue in the oral cavity, the higher concentration is safe.

The present invention is based on the discovery that a convenient and safe method exists for direct application of solutions of concentrated hydrogen peroxide to the enamel including incidentally to the gingiva and other soft tissue, utilizing an aerosol spray. Since the tooth whitening art for well over 100 years has believed otherwise, the present invention teaches, for the first time, that indeed the use of these previously-deemed unsafe oral liquid compositions of concentrated hydrogen peroxide can be employed safely as demonstrated by the results shown in Tables 1 and 2. It is this employment of solutions of higher concentration of hydrogen peroxide, as an aerosol spray, that gives rise to the desired teeth-whitening efficacy. In many cases the whitening action has been demonstrated (see Table 3 and Table 4) as comparable to or better than the other methods (strip, tray gel, paint on gel), and much better than the tooth whitening rinses, including the spray forms of the prior art using low concentrations, or tooth whitening toothpastes. Thus, the present invention teaches to the art of tooth bleaching, a novel means to whiten teeth with results as good as or better than the existing methods, but with the advantages of quick-action, and of convenience and facile use engendered by the employ of oral spray.

TABLE 3

DETERMINATION OF TOOTH WHITENING PROPERTIES
OF A 12.5% HYDROGEN PEROXIDE SPRAY,
TWO WEEKS OF USAGE, TWICE DAILY

| SUBJECT | CHANGE* |
|---|---|
| 1 | 3 |
| 2 | 5 |
| 3 | 7 |
| 4 | 5 |
| 5 | 7 |

*Changes are based on the Vita Shade Guide as shade guide units, +Δsgu.

The results show conclusively that a preferred embodiment of the present invention, a spray tooth whitener having a concentration of peroxide of 12.5%, when used twice daily for 10-14 days give rise to whitening of readily noticeable proportions, on the order of 3-7+Δsgu.

TABLE 4

DETERMINATION OF TOOTH WHITENING PROPERTIES
OF A 35% HYDROGEN PEROXIDE SPRAY,
ONE 2 MINUTE TREATMENT

| SUBJECT | CHANGE* |
|---|---|
| 1 | 5 |
| 2 | 7 |
| 3 | 7 |
| 4 | 3 |
| 5 | 6 |
| 6 | 4 |
| 7 | 8 |
| 8 | 7 |
| 9 | 8 |
| 10 | 8 |

*Changes are based on the Vita Shade Guide as shade guide units, +Δsgu.

Table 4 provides data that demonstrate conclusively that a preferred embodiment of the present invention, where an aerosol spray method employing a solution of hydrogen peroxide bleach of 35% concentration and including the apparatus of the present invention similar to those depicted in FIGS. 6A-D, is very effective in whitening the teeth with just one 2-minute application. These results are similar to those expected for the vital bleaching technique after one treatment, but in stark contrast to what would be expected based on current knowledge of the tooth whitening art; that is that such efficacy may be achieved without harm to the patient, and without the employ of a dam to protect the gingiva and other soft tissue, and without the need for professional technician to apply the treatment.

The aerosol spray method of the present invention serves to deliver hydrogen peroxide to the teeth in higher dosages than, due to safety concerns, were previously believed possible by those skilled in the art. It has been discovered that it is this spray method that provides the aerosol chemistry that allows for the safe application of hydrogen peroxide of higher concentration to the hard tissue present in the oral cavity, without the need for a dam to protect the gingiva and other soft tissue, and without the discomfort typically encountered for other tooth whitening techniques that use high concentrations of hydrogen peroxide.

A possible explanation for this discovery is twofold. First, the greater surface area of the small aerosol droplets in the spray, in comparison to the bulk liquid (as a solution or large droplet), provides a much greater exposure of highly reactive external peroxide moieties to the target tissues. This results in a higher effective concentration of peroxide interfacing with the saliva, where catalytic enzymes present to decompose the peroxide into the active oxygen are highly prevalent. Thus, the tiny droplets serve to facilitate an increased rate of reaction of the reactant peroxide, as an enzyme substrate, to the bleaching (and bactericidal) product, oxygen. Secondly, by administering concentrated hydrogen peroxide solutions to the mouth as tiny aerosol droplets, these small droplets bind with the hard tissue (enamel) to instantly release a concentrated flash of hydrogen peroxide (or oxygen), but to the soft tissue and non-target mucosal areas of the oral cavity, however, they get mixed with the saliva and quickly become diluted, thus forming, in situ, oral solutions of hydrogen peroxide to levels known to be safe. This latter explanation may provide some rationale why the present invention teaches the unprecedented safety engendered to spray liquid hydrogen peroxide oral rinse compositions having much greater tooth bleaching concentrations, where these concentrations are at levels previously believed to be harmful for use in the human oral cavity.

A first alternative process of the present invention is the incorporation, as a pretreatment, of the use of the plaque removal/antiplaque oral compositions and methods taught by Arnold. Specifically, these fundamental and core plaque removal/anti plaque compositions are comprised of a an effervescent tablet or effervescent powder composition for oral use having a non-aqueous, water soluble, pharmaceutically acceptable carbon dioxide source; a plaque adsorbent and a non-aqueous, water soluble, pharmaceutically acceptable acid source. The carbon dioxide source is preferably carbonate and/or a bicarbonate source, more preferably a bicarbonate salt, carbonate salt and mixtures thereof. The plaque adsorbent is preferably a silica source and more preferably silica, silicon dioxide, alumina, aluminosilicate, sodium aluminum silicate, zirconium silicate and mixtures thereof. The acid source is preferably a fruit acid source and more preferably a citric or tartaric acid. The presently preferred choice and ratio of these agents in the core and fundamental plaque removal/antiplaque compositions are; about 50-90 parts bicarbonate source, about 10-90 parts silica source and about 2-20 parts fruit acid, more preferably; about 60-85 parts bicarbonate source, about 20-80 parts silicon dioxide source and about 3-15 parts fruit acid source and most preferably; about 65-80 parts bicarbonate source, about 25 to 60 parts silica source and about 4-10 parts fruit acid.

As will be seen in EXPERIMENT V below the pretreatment procedure is to use it before the aerosol bleaching treatment by vigorously swirling the pretreatment composition in a salivary mixture around the oral cavity and then expectorating (the terms expelling and expectorating are synonymous). The pretreatment can be expectorated or swallowed.

Xylitol is also a preferred ingredient, and with respect to the above described core plaque removal/antiplaque composition, the preferred ratio of xylitol in this plaque removal/antiplaque core composition is from about 1-20 parts xylitol, to about 1-10 parts of the core composition, more preferably from about 2-15 parts xylitol to about 1-10 parts of the core composition, and most preferably from about 5-10 parts xylitol to about 1-8 parts core composition.

The composition is prepared such that upon usage, the salivary pH remains in the basic range.

The method for using the above described first alternative is to use the plaque removal/antiplaque treatment no more than about 15 minutes before the tooth whitening treatment in order to obtain optimum synergistic effect of the two treatments, and the closer in time, the better.

Practice of this first alternative provides for a more efficient, and in many cases, improved overall tooth-whitening result, as well as an enhancement to the overall chemotherapeutic benefits engendered by the daily practice of the present invention. This embodiment is provided in order to aid in the removal of biofilm, which contains organic and inorganic accumulates referred to as dental plaque from the enamel and gingiva, and to aid in the removal of food and drink residues and tobacco staining agents. It is these agents that ultimately are the source of discolor for the teeth, and the source of periodontal diseases. The enhancement to the spray tooth whitening technique disclosed by the present invention, is also due to a chemical catalysis of the bleaching reaction, which aids the decomposition of hydrogen peroxide to the active bleaching oxygen moieties. A proposed mechanism for these improved effects is rationalized as follows. The use of the effervescent bicarbonate-based compositions as a pretreatment oral rinse results in significant debridement of the oral cavity, and thus serves to expel from the oral cavity pellicle-bound food debris residues, plaque residues and general oral mucosa (referred to as "biofilm"). Such debridement provides for cleaner and more accessible surfaces on the enamel (hard tissue [teeth]). Since this debridement action, which results immediately upon the practice of this first alternative, removes much of the biofilm that encases the surfaces of the teeth, it allows for a more rapid and thorough and more uniform penetration of the bleaching solution onto the surfaces of the enamel, and into the pores of the teeth. Since the degree of tooth whitening is a direct consequence of the amount of peroxide or oxygen that is exposed to the internal and external surfaces of the tooth, this cleaning of the surfaces of the enamel serves to increase the rate and degree of tooth whitening.

The enhancement to the tooth whitening action of the aerosols of the present invention as a result of practice of the first alternative is not only due to the debridement action that occurs on the surface of the teeth, but also due to the catalysis of the bleaching chemical reaction. By incorporating the antiplaque composition as the first alternative, catalysis of the bleaching reaction may be achieved due to the sustained presence of catalytic moieties on the surface of the teeth. Specifically, bicarbonate ion as well as inorganic micronsized particles has a sustained residence on the surfaces of the teeth, and in the biofilm residues encasing the teeth, and coating the inner oral soft tissues as a direct result of the practice of the antiplaque methods and compositions taught by Arnold. It is well known that most transition metal salts, as well as trace metals, many of which are found in the silicon-dioxide polymers of the teachings of Arnold, catalyze the rapid decomposition of hydrogen peroxide to products suitable as bleaching agents (oxygen, per oxygen, hydroxide free radicals, superoxide). Thus, sustenance of these types of particles gives rise to sustenance of catalytic moieties on the surfaces important to tooth whitening bleaching reactions. By having bicarbonate ion sustenance, a chemical microenvironment is created on the surface of the teeth, gums and inner oral soft tissues, having a pH in the slightly basic range, and this mildly basic pH is well known to enforce as a strong catalysis for the decomposition of hydrogen peroxide to active bleaching components. This sustained local basic pH found on the surfaces of the enamel, gingiva and in the saliva, is sustained on the order of many minutes, and has been demonstrated, the results of which are described as follows. This is more fully explained in conjunction with Example VIII below. In summary, it is the: (1) pre-cleaning and removal of the biofilm (debridement); (2) buffering, in the slightly basic range of the inner oral cavity, and; (3) the sustained presence of catalytic inorganic residues, that provides for greater activity of the peroxide moiety and, hence, faster and more aggressive tooth whitening as a result of the practice of the first alternative to the present invention.

While this first alternative is described with reference to the high concentration aerosol spray invention, it can used beneficially as a pretreatment for any tooth whitening process that uses hydrogen peroxide, and the same applies to the other alternatives described below.

An embodiment of such a series is repeating of the tooth whitening treatment for a plurality of times, each time being separated by at least about eight hours. A further embodiment is combining of this series with the pretreatment described above.

A second alternative to the present invention is the practice of the tooth whitening procedure in a series, and shortly before each tooth whitening treatment, the protocol and compositions described above for the first alternative are employed as pretreatments for the tooth whitening. A preferred series is once a day for several days.

A third alternative utilizes the teachings described for the second alternative for use in between the series of tooth whitening treatments. This therefore, provides an additional plaque removal/antiplaque treatment not proximate to the tooth whitening treatments of the series (such as once a day), but at a time approximately, insofar as convenient, half-way between them. This third alternative is important for tooth whitening maintenance, since its practice contributes to the overall reduction in biofilm. As a direct result of the use of the plaque removal/antiplaque compositions of Arnold in between tooth whitening treatments, plaque, organic and inorganic colorant agents from food, drink, bacteria are reduced significantly. Since it is these agents which are the ultimate causes of the discoloration of the teeth, and are the targets of the whitening action, it follows that the less amount of these that are present in the oral cavity and on the surfaces of the enamel to be bleached that, by practice of the third alternative, a more efficient tooth bleaching process may be achieved. It is also to be noted that this third alternative may be employed for tooth whitening treatment protocols, in general, that is, it is not limited to the spray aerosol techniques taught by the present invention.

It is believed that a synergy exists that enhances the chemotherapeutic properties of the present invention, as well as its cosmetic tooth whitening properties. Such synergy exists between the aerosol spray tooth whitening compositions of the present invention, and the plaque removal/antiplaque pretreatment compositions when they are used in closely timed sequence. The rapid release of oxygen catalyzed by the practice of the first alternative also facilitates the chemotherapeutic properties of the present invention. That is, utilizing the first and second alternatives, in addition to the novel and effective tooth whitener, it functions as an effective agent for the prevention and remediation of periodontal diseases and halitosis, and for general maintenance of oral aesthetics.

Cosmetically, the present invention teaches that a significant synergistic enhancement takes place as a result of employment of the first and second alternatives of the present invention. As discussed above, this enhanced tooth whitening efficacy in comparison to the embodiment of the present invention where the aerosol spray tooth whitening treatment is used alone, is most likely due to: 1) an appreciable pre-cleaning and removal of the biofilm (debridement); (2) buffering, in the slightly basic range of the inner oral cavity, and; (3) the sustained presence of catalytical inorganic residues. These factors allow for a more penetrative oxygenation of the enamel, and a more active bleaching reaction. Increasing the rate of the bleaching reaction, and the degree of the bleaching reactions effectiveness gives rise to a more aesthetic result in a shorter period of time.

Chemotherapeutically, the methods and compositions of the present invention utilizing the first, and second alternatives, affords to the present invention an enhanced, synergistic method for the remediation and prevention of periodontal diseases, gingivitis, and halitosis than previously anticipated (by the teachings of Arnold, and also from the vast amount of research reported for chemotherapeutic benefits of the Keyes technique). The teachings of the present invention that safe application to the human oral cavity of higher-strength hydrogen peroxide solutions in combination with the first and second alternatives, provide for a more orally active biological treatment than previously thought possible by practice of the Keyes methodology, or by the teachings of Arnold, exclusively. The degree of chemotherapeutic efficacy engendered by these methods was restricted by safety concerns. However, as a direct consequence of the teachings of the first, second and third alternatives, and that of the unprecedented application of highly active hydrogen peroxide solutions to target surfaces on the teeth and in the gum tissues and pockets as taught by the aerosol compositions of the present invention, a much greater chemotherapeutic activity is realized in a safe and efficacious manner. Before the teachings described herein (by the present invention) the chemotherapeutic efficacy engendered by these methods was limited by safety concerns, since they had to incorporate mouth rinse solutions of hydrogen peroxide less than 3%—considered as maximum that could be used without causing harm to the user (prior to the present invention). Enhanced oral chemotherapeutic efficacy is believed to be due to the substantially increased oral action of the peroxide moiety in its more concentrated form (5%-40%) in the targeted areas of the infected gingiva, the periodontal pockets. It is well known that bactericidal effects of hydrogen peroxide are a direct consequence of the effective concentration of the peroxide moiety. Delivery of hydrogen peroxide of high strength locally and directly to the membrane of injure, in much higher concentrations than previously deemed safe, on the order of 3 to 10 times higher ($[H_2O_2]$=5%-40%) than the hydrogen peroxide solutions heretofore-deemed safe for use as liquid preparations ($[H_2O_2]$=0.5%-3%). It is this application of high-strength peroxide solution directly to the gingival surfaces, and this presence in combination with the bicarbonate ion sustansivity as a result of the practice of the first alternative, provides for a more aggressive bactericidal activity than previously obtainable. This results in a significantly improved chemotherapeutic treatment for prevention and remediation of periodontal diseases and halitosis. Also, the incorporation of the first and second alternatives to the present invention imparts a substantial pH buffer to the oral cavity, and this is thought to help mitigate any unwanted demineralization of the tooth surface due to the oral presence of digestive acids, or acidic oral residues, or tooth whitening bleaches. The present invention, therefore, teaches a more facile and more effective chemotherapeutic method and composition for treatment of the gingival tissue with peroxide and bicarbonate salts in comparison to the Keyes technique; and in comparison to those derivatives of Keyes technique that are practiced routinely in many periodontal clinics and patient homes throughout the world; and also in comparison to the many traditional "out of the clinic" (in home) treatments such as bactericidal mouthwashes, toothpastes, tongue scrapers, breath lozenges and breath sprays, and picks, etc. which are commonly used in the oral care practices of modern day.

The compositions of the first, second and third alternatives of the present invention include the anti plaque compositions of the teachings of Arnold. Preferred are compositions described as the preferred embodiments of said teachings. These are comprised of a carbonate source and/or a bicarbonate source, preferably sodium bicarbonate and/or potassium bicarbonate, a fruit acid source, preferably citric or tartaric acid, and a source of silicone dioxide, preferably amorphous silica, and most preferably, precipitated amorphous silica. Xylitol is also a preferred ingredient. Flavoring agents and surfactants may also be included. It is anticipated that other agents may be included.

The preferred amount of carbonate and/or bicarbonate source is from about 3% to about 90%, more preferably from about 8% to about 80%, more preferably from about 10% to about 60%, and most preferably from about 10% to about 45%. The preferred amount of fruit acid source is from about 0.5% to about 22%, more preferably from about 1.25% to about 18%, more preferably from about 1.5% to about 8%, and most preferably from about 2% to about 11%. The preferred amount of silica is from about 1% to about 60%, more preferably from about 4% to about 50%, more preferably from about 6% to about 35%, and most preferably from about 10% to about 45%. The preferred amount of Xylitol is from about 5% to about 97%, more preferably from about 8% to about 85%, more preferably from about 10% to about 80%, and most preferably from about 10% to about 70%.

EXAMPLES OF COMPOSITIONS OF THE INVENTION AND METHODS OF USE THEREOF

Example I

The following describes an example of a preferred embodiment of the present invention that is effective in whitening of the teeth using one treatment.

High Strength Treatment—One Treatment Protocol.

| INGREDIENT | AMOUNT |
| --- | --- |
| Hydrogen Peroxide solution (ca 35%) FMC | 1000 grams |

Figure 6A:
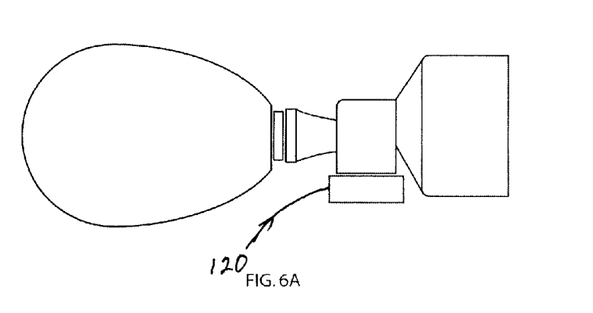
FIGS. 6A, 6B, 6C and 6D are views of another mouthpiece.
Figure 6B:
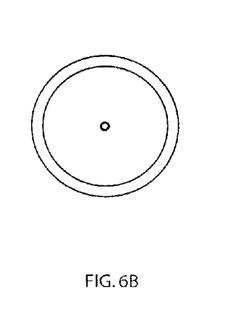
Figures 6C, 6D:
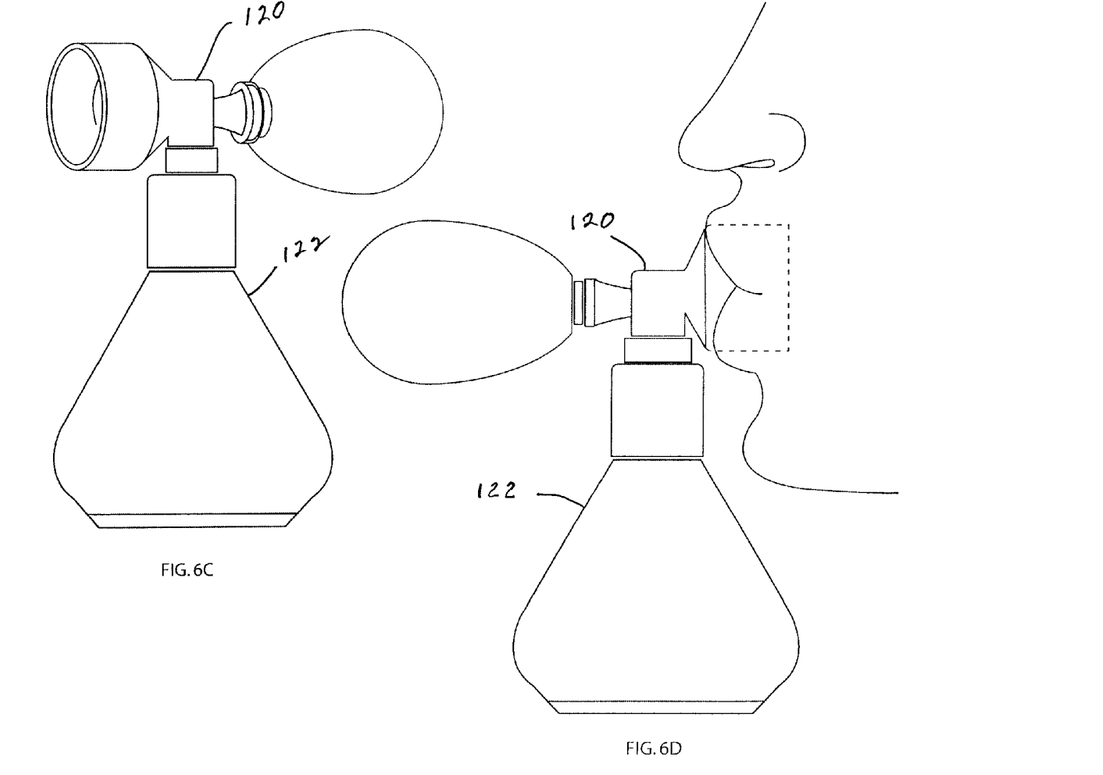

The commercially available hydrogen peroxide 35% aqueous solution was poured directly into an atomizer, similar to that displayed in FIG. 6. The mouthpiece was then attached, and then holding the apparatus with two hands, one holding the mouthpiece and the other hand ready to squeeze the atomizer bulb, the mouthpiece was inserted into the oral cavity, where the mouth was closed such that the upper and lower arrays of teeth were touching. The mouthpiece portion of the mouthpiece-atomizer apparatus was then inserted into left quarter of the front portion of the mouth with the lips surrounding the outer portion of the mouthpiece so that fluid could not be ejected from the closed mouth. Then, the atomizer bulb was pumped 3 times. Then, the position of the apparatus was changed by moving to the center portion of the mouth, then the bulb was pumped an additional 3 times, and finally, the position of the mouthpiece-atomizer apparatus was changed, moving from the center to the right portion of the mouth, and again, 3 pumps of the atomizer by depressing and releasing the fingers in the holding hand, was undertaken, and then the apparatus was removed from the mouth, and the lips tightly closed. This spray operation was completed in about 10 seconds. A slight tingling sensation was reported, but no pain or burning or any injury was observed, or reported. After the lips were sealed, a bountiful effervescence took place and in concert with this effervescence, the subject gently swirled the salivary mixture throughout the oral cavity for about 2 minutes, then expectorated. The subject was measured for change in whitening with the Vita Shade Guide, and the result was a difference of 6 shades, +Δsgu. No pain to the gingival or soft tissue was observed or reported, subsequently.

Example II

The following example describes a preferred tooth bleaching treatment procedure useful in achieving a high degree of whitening within a short period of time.
High Strength Treatment—Multi Treatment Protocol

| INGREDIENT | AMOUNT |
| --- | --- |
| Hydrogen Peroxide solution (ca 35%) FMC | 1000 grams |

The commercially available hydrogen peroxide 35% aqueous solution was poured directly into an atomizer reservoir, similar to that displayed in FIG. 6. The mouthpiece was then attached, and then holding the apparatus with two hands, one holding the mouthpiece, and the other hand ready to squeeze the atomizer bulb, the mouthpiece was inserted into the oral cavity, where the upper and lower jaws where closed such that the upper and lower arrays of teeth were touching. The mouthpiece portion of the mouthpiece-atomizer apparatus was then inserted into left quarter of the front portion of the mouth with the lips surrounding the outer portion of the mouthpiece so that fluid could not be ejected from the closed mouth. Then, the atomizer bulb was pumped 3 times. Then, the position of the apparatus was changed by moving to the center portion of the mouth, then the bulb was pumped an additional 3 times, and finally, the position of the mouthpiece-atomizer apparatus was changed, moving from the center to the right portion of the mouth, and again, 3 pumps of the atomizer by depressing and releasing the fingers in the holding hand, was undertaken, and then the apparatus was removed from the mouth, and the lips tightly closed. This spray operation was completed in about 10 seconds. A slight tingling sensation was reported, but no pain or burning or any injury was observed, or reported. After the lips were sealed, a bountiful effervescence took place and in concert with this effervescence, the subject gently swirled the salivary mixture throughout the oral cavity for about 2 minutes, then expectorated.

This procedure was carried out once a day for 7 consecutive days. The subject was measured for degree of whitening using the Vita Shade Guide. A value of 9 shades+Δsgu was determined for the degree of whitening value.

Example III

The following example describes a preferred embodiment of the present invention, where a sequence of tooth whitening operations is employed using different strengths of aerosol mixtures of hydrogen peroxide solutions.
Sequence Use of High Strength in Combination with Lower Strength Aerosol Mixtures
A. Preparation of High Strength Bleaching Solution

| INGREDIENT | AMOUNT |
| --- | --- |
| Deionized Water | 50 grams |
| Hydrogen peroxide solution (ca. 35%, FMC) | 950 grams |

B. Preparation of Lower Strength Bleaching Solution

| INGREDIENT | AMOUNT |
| --- | --- |
| Deionized Water | 670 grams |
| Hydrogen peroxide solution (ca. 35%, FMC) | 350 grams |

The protocol employs sequential use of preparation A and B according to the sequence of: one day, once a day, of preparation A followed by three days, once each day, of preparation B, then repeating for a total of 24 days (6 rounds). The teeth were measured for whiteness using the Vita Shade Guide, and a change of 10 shades, +Δsgu, of whitening was determined. No pain or injury was reported, or observed.

Example IV

The following example is provided to illustrate a tooth whitening method using the lower strength aerosol spray composition in a sequential, multi day dosage regimen.

The following bleaching solution was prepared, and then a hand held 4 oz aerosol spray device similar to that described in FIG. 1 was charged with the solution.

| INGREDIENT | AMOUNT |
| --- | --- |
| Deionized Water | 650 grams |
| Hydrogen peroxide solution (ca. 35%, FMC) | 315 grams |

The tooth whitening protocol described in Example I. was carried out once a day for 30 consecutive days. The result was a change in shade of 7 shades.

Example V

The following example is provided to illustrate the action of the First Alternative.

First Alternative (Pre-Treatment) with High Strength Bleaching Solution
Preparation of Solid Oral Preparation (V), as a Powder, of the First Alternative

| INGREDIENT | AMOUNT |
| --- | --- |
| Xylitol | 2000 grams |
| Citric acid | 100 grams |
| Silicon Dioxide | 569 grams |
| Sodium Bicarbonate | 1075 grams |
| l-Menthol | 30 grams |
| Spearmint oil | 2.5 grams |

First, at about 15 minutes before spray bleaching treatment, 2 grams of the powder form of the composition described above for the Solid Oral Preparation V., was placed on the tongue, and then the lips were closed and the resulting salivary mixture was vigorously swirled around the inner oral cavity using the tongue to massage the gums, and the teeth, then after about 1 minute, the subject expectorated. After about 15 minutes The High Strength Bleaching Solution of Example I was poured into the atomizer of FIG. 6, and then using the procedure described in EXAMPLE I., the aerosol was sprayed directly onto the front surfaces of the teeth and the whitening procedure undertaken. The subject expectorated, and the subject's teeth were evaluated for degree of whitening enhancement, and the change was determined to be 7 shades.

Example VI

The following example is a description of the Second Alternative teaching of the present invention.
Tooth Whitening Protocol where Pretreatment Using Compositions of Arnold Before the Spray Tooth Whitening Treatment.
Pre-treatment Solid Oral Preparation VI.

| INGREDIENT | AMOUNT |
| --- | --- |
| Xylitol | 2000 grams |
| Citric acid | 25 grams |
| Silicon Dioxide | 75 grams |
| Sodium Bicarbonate | 200 grams |
| LoHan | 0.1 grams |
| l-Menthol | 30 grams |
| spearmint oil | 2.5 grams |

Two grams of the powder form of the composition described above for the Solid Oral Preparation, was placed on the tongue, and then the lips were closed and the resulting salivary mixture was vigorously swirled around the inner oral cavity using the tongue to massage the gums, and the teeth, then after about 1 minute, the subject expectorated. After about 15 minutes, The Lower Strength Bleaching Solution described in Example III and corresponding atomizer apparatus was charged and then using the procedure described in EXAMPLE I., the aerosol was sprayed directly onto the front surfaces of the teeth and the whitening procedure undertaken. This sequence of pre treatment with a solid oral preparation of Arnold followed by spray tooth whitening treatment was repeated every day, once a day, for 1 month.

The subject was evaluated for tooth whitening and it was determined the subject had a shade change of 9 units.

Example VII

The following example illustrates the use of the Third Alternative of the present invention.

The compositions and methods described for pre treatment, and for treatment, as described by EXAMPLE VI, were carried out over the course of 30 days. In addition, the Solid Oral Preparation described by EXAMPLE VI was administered in between tooth whitening treatments. Typically, the subject used the solid oral preparations of Arnold about 3 hours after the treatment. The subject noticed an overall appealing feeling to the condition of the oral cavity, and his fellow associates commented on how less odiferous his breath appeared to them, and how white his teeth looked.

Example VIII

This example provides another example of the use of the compositions of Arnold employed as the Third Alternative of the present invention.

The solid oral preparation described in EXAMPLE V was prepared. The tooth whitening composition and apparatus were prepared according to EXAMPLE II, and the method of EXAMPLE II was carried out for the course of 7 days. During this time period, intermittently, random times between tooth whitening operations, the use of the solid oral preparations described in EXAMPLE V (anti plaque effervescent composition), and the oral rinse procedures described therein, were operational, and carried out at least once a day for the 7 day period. The subject continued to use the solid oral preparations random times over the course of many months, whenever the subject felt the need to cleanse the oral cavity, and whenever the subject was unable to brush the teeth using traditional tooth brushing methods. During this period, the subject also used the lower strength bleaching solution described in EXAMPLE III at random times to occasionally bleach the teeth and obtain a slightly whiter shade of the enamel. The results were a much healthier condition of the gums, and an enhanced whitening of the teeth.

Example IX

Clinic Study of pH Changes after Use of Antiplaque Composition

In the study 10 subjects were evaluated for pH changes over time after use of the composition set out below which is an embodiment of the Arnold antiplaque and plaque removal technology.
The following plaque removal/antiplaque oral composition was prepared.
Pre-Treatment Solid Oral Preparation IX

| INGREDIENT | AMOUNT |
| --- | --- |
| Xylitol | 100 grams |
| Citric acid | 25 grams |
| Silicon Dioxide | 75 grams |
| Sodium Bicarbonate | 200 grams |
| LoHan | 0.1 grams |
| l-Menthol | 30 grams |
| Spearmint oil | 2.5 grams |

Figure 7:
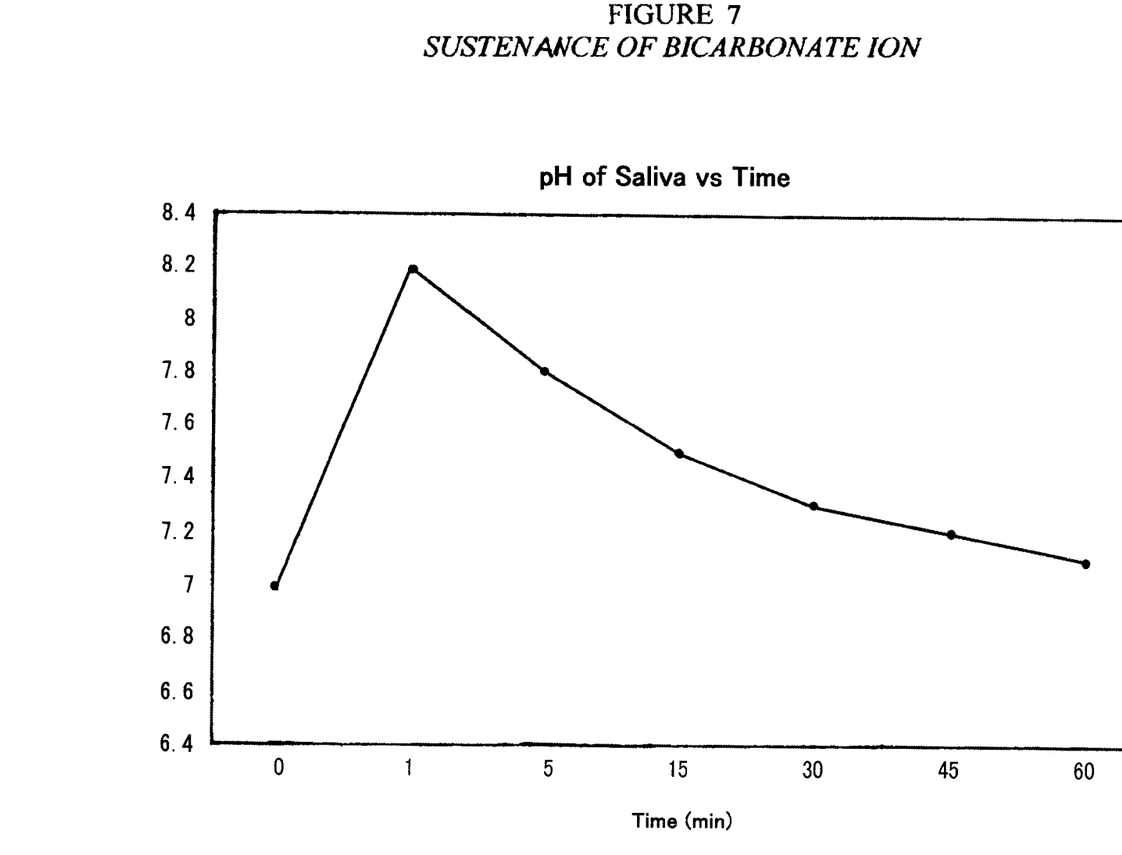
FIG. 7 is a graph showing the sustenance of the bicarbonate ion in a salivary mixture.

FIG. 7 provides results of a clinical study where 10 subjects were evaluated for pH changes over time after use of a preferred embodiment of the teachings of Arnold as detailed in Example IX. Saliva samples of the subjects were collected, and the pH measured (time=0 min). Then, each subject was treated with the effervescent composition of Arnold, and expectorated after swishing the resulting salivary mixture for 2 minutes. The pH reading of collected saliva samples were recorded for the collection times of 1 min, 5 min, 15 min, 30 min and 1 hour. The increase into the basic ph range of the saliva pH, and its sustained basic values over 15 minutes, and to 30 and 60 minutes are evident. The basic pH is directly due to the bicarbonate ion having substantial concentration in the salivary mixture sample measured. Such sustenance of the bicarbonate ion is a direct result of the presence of is micronsized silicon dioxide particles and bicarbonate salt particles that are sustained in the oral cavity after oral rinse procedure of Arnold is completed. The presence of the bicarbonate ion directly on the surface of the teeth and gums, and to the saliva, creates a local chemical environment on these oral surfaces where a pH buffer is in effect. This buffer is between pH 7.4 and pH 8.2, pH conditions known to enforce rapid catalysis of peroxide decomposition, and thus activate the peroxide bleach for the tooth whitening action.

In summary, the present invention teaches a convenient, unprecedented method, compositions and devices, which provide highly active and effective cosmetic and pharmacological benefits for the human oral condition, specifically for whitening of the teeth, and for the remediation and prevention of periodontal diseases and bacterial halitosis. It is also noteworthy that the portability and convenience of the present invention renders it easy to use often during the course of the day or evening. It is this high frequency of use of the cleansing and bactericidal compositions of the present invention that facilitates both an enhancement to the oral cosmetic tooth-whitening efficacy as well as promotes higher levels of oral pharmacological health. The pharmacological efficacy of the present invention is much improved in comparison to modern day portable and non-portable preventative and remedial oral care treatments, which are available over counter (OTC) as drugs, and in many cases, on magnitude of efficacy reached by clinical treatments, or physician-directed prescriptive measures. The liquid spray method has many advantages to other in-home tooth whitening methods, with at worst, similar sensitivity expected for any tooth-whitening product (mild sensitive to the soft tissue—readily reversible within minutes). The present invention has an advantage to the gels and strip methods, since the present invention is much more convenient and discrete to use, and much more portable, and most importantly, much faster in its tooth whitening action. This results in a more frequent usage with much less discomfort to the user, thus facilitating a more pleasing and desirable tooth whitening and oral cleaning and deodorizing experience.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

The invention claimed is:

1. A method for whitening teeth consisting of;
providing an aqueous solution consisting of a concentration of hydrogen peroxide of from about 6% to about 37% by weight;
delivering the solution into the oral cavity of a user as an aerosol spray so that the aerosol spray is directed at the user's teeth and said aerosol spray having direct and immediate whitening effect on the user's teeth and without regard to incidental contact of the spray on the user's gums or other oral tissue, and thereby creating a saliva mixture containing the hydrogen peroxide;
expelling the resulting saliva mixture.

2. A method for whitening teeth with a hydrogen peroxide spray solution as a tooth whitening procedure consisting of:
delivering into the oral cavity of a user as an aerosol spray, an aqueous solution consisting of water and hydrogen peroxide having a concentration of hydrogen peroxide of about 6% to 37% by weight
whereby the aqueous solution is delivered having direct and immediate whitening action on the user's teeth and without regard to incidental contact of the solution on the gums or other oral tissue, thereby creating a saliva mixture containing the hydrogen peroxide; and expelling the resulting saliva mixture.

3. A method for whitening teeth with a hydrogen peroxide spray solution as a tooth whitening procedure consisting of:
delivering an aqueous solution as an aerosol spray into the oral cavity of a user including contact with the user's teeth, having direct and immediate whitening effect on the user's teeth and without regard to incidental contact of the solution on the gums or other oral tissue, the aqueous solution consisting of water and hydrogen peroxide having a concentration of hydrogen peroxide of about 6% to 37% by weight, thereby creating a saliva mixture containing the hydrogen peroxide; and expelling the resulting saliva mixture.

* * * * *